US007888074B2

(12) United States Patent
Ehricht et al.

(10) Patent No.: US 7,888,074 B2
(45) Date of Patent: Feb. 15, 2011

(54) MICROCHIP MATRIX DEVICE FOR DUPLICATING AND CHARACTERIZING NUCLEIC ACIDS

(75) Inventors: Ralf Ehricht, Jena (DE); Thomas Ellinger, Jena (DE); Jens Tuchscherer, Jena (DE); Eugen Ermantraut, Jena (DE); Siegfried Poser, Jena (DE); Torsten Schulz, Jena (DE)

(73) Assignee: Clondiag Chip Technologies GmbH, Jena (DE)

( * ) Notice: Subject to any disclaimer, the term of this patent is extended or adjusted under 35 U.S.C. 154(b) by 0 days.

(21) Appl. No.: 10/038,284

(22) Filed: Jan. 2, 2002

(65) Prior Publication Data

US 2002/0150933 A1 Oct. 17, 2002

Related U.S. Application Data

(63) Continuation-in-part of application No. PCT/EP00/06103, filed on Jun. 30, 2000.

(30) Foreign Application Priority Data

Jul. 2, 1999 (DE) ................................ 199 32 423

(51) Int. Cl.
*C12P 19/34* (2006.01)
*C12M 1/36* (2006.01)
*G01N 15/06* (2006.01)

(52) U.S. Cl. ................ 435/91.2; 435/283.1; 435/287.2; 422/68.1; 422/82.05

(58) Field of Classification Search ..................... 435/6, 435/283.1, 287.2, 288.4, 288.5; 422/68.1, 422/109, 129, 131, 138
See application file for complete search history.

(56) References Cited

U.S. PATENT DOCUMENTS 5,222,808 A * 6/1993 Sugarman et al. ........... 366/274
5,475,610 A * 12/1995 Atwood et al. .............. 700/269
5,744,101 A * 4/1998 Fodor et al. ................. 422/131
5,856,174 A * 1/1999 Lipshutz et al. .......... 435/286.5
5,882,903 A * 3/1999 Andrevski et al. ......... 435/91.2

(Continued)

FOREIGN PATENT DOCUMENTS

EP 0 840 113 A2 5/1998
WO 95/33846 12/1995
WO 99/09042 2/1999

OTHER PUBLICATIONS

Academic Press Dictionary of Science and Technology, ed. C. Morris, Academic Press, San Diego, 1992, p. 1768.*
English-language Abstract for DE 19940750.
English-language Abstract from PCT/DE99/03400, published as WO 00/25171 (Equivalent to DE 19850225).
Burns, Mark A., "Microfabricated structure for integrated DNA analysis", *Proceedings of the National Academy of Sciences USA*, 93(11), (May 1996),5556-5561.

*Primary Examiner*—B J Forman
(74) *Attorney, Agent, or Firm*—Steptoe & Johnson LLP

(57) ABSTRACT

The aim of the invention is to provide a device for duplicating and characterizing nucleic acids almost simultaneously and with a high sample throughput rate. The device consists of a chamber body with a recess whose edge sealingly holds an optically transparent chip. Said chip holds nucleic acids in individual spots on a detection surface. The chamber body is placed on an optically transparent chamber support with a bearing surface, in such a way that a capillary gap, which can be filled with a liquid sample, is formed between the detection surface of the chip facing towards the chamber support and said chamber support. The chamber body is provided with an inlet and an outlet, which are spatially separate from each other, and has a space, which laterally encompasses the chip and which has a gas reservoir. The chamber support is provided with heating elements.

18 Claims, 10 Drawing Sheets

U.S. PATENT DOCUMENTS

| | | | | | |
|---|---|---|---|---|---|
| 5,922,604 | A | * | 7/1999 | Stapleton et al. | 436/46 |
| 6,054,277 | A | | 4/2000 | Furcht et al. | 435/6 |
| 6,093,370 | A | * | 7/2000 | Yasuda et al. | 422/68.1 |
| 6,126,400 | A | * | 10/2000 | Nichols et al. | 416/241 B |
| 6,126,899 | A | * | 10/2000 | Woudenberg et al. | 422/50 |
| 6,140,044 | A | | 10/2000 | Besemer et al. | 435/6 |
| 6,284,195 | B1 | | 9/2001 | Lai et al. | 422/58 |
| 6,296,752 | B1 | * | 10/2001 | McBride et al. | 204/547 |
| 6,303,288 | B1 | | 10/2001 | Furcht et al. | |
| 6,521,181 | B1 | * | 2/2003 | Northrup et al. | 422/52 |
| 6,642,046 | B1 | | 11/2003 | McGarry et al. | 435/287.2 |
| 6,664,104 | B2 | | 12/2003 | Pourahmadi et al. | 435/288.6 |

* cited by examiner

MICROCHIP MATRIX DEVICE FOR DUPLICATING AND CHARACTERIZING NUCLEIC ACIDS

RELATED APPLICATIONS

This application is a continuation-in-part under 35 USC 111(a) of International Application No. PCT/EP00/06103, filed in German on Jun. 30, 2000 and published as WO 01/02094 A1 on Jan. 11, 2001, which claimed priority under 35 U.S.C. 119 from German Application No. 199 32 423.9, filed Jul. 2, 1999, which applications are incorporated herein by reference.

The invention relates to a device for duplicating and characterizing nucleic acids.

It has been known for decades that the amplification (duplication) of deoxyribonucleic acid (DNA), the molecules encoding the genome (the hereditary information) of organisms, ensues in vivo (within the cell) by transcription, and can be conducted in vitro (outside of the cell) by the polymerase chain reaction (PCR) method.

In the meantime, it has become a laboratory standard to duplicate nucleic acids by PCR, to clone the PCR products (to integrate same in a carrier molecule and to introduce it into a microorganism), to amplify the cloned PCR products in microorganisms and to isolate the amplified PCR products (Sambrook, J; Fritsch, E. F and Maniatis, T, 1989, Molecular cloning: a laboratory manual 2$^{nd}$ edn. Cold Spring Harbor, N.Y., Cold Spring Harbor Laboratory). Said two-stage routine amplification allows for generating from some few initial nucleic acid molecules an enormously high number of identical molecules, but has the disadvantage of being highly laborious and time-consuming, featuring a low sample throughput (the number of nucleic acids processed per time unit), and thus being very cost-intensive.

The one-stage amplification by PCR, however, is relatively fast, enables a high sample throughput by miniaturized processes in small preparation volumes, and is not so labour-intensive due to automated processing.

A characterization of nucleic acids by a mere amplification is not possible. It is on the contrary necessary to use analytical methods subsequent to the amplification, such as nucleic acid sequence determination or electrophoretic examinations of the PCR products or the individual fragments thereof produced enzymatically, for characterizing the PCR products.

From the documents U.S. Pat. No. 5,716,842; DE 195 19 015 A1; WO 94/05414; U.S. Pat. No. 5,587,128; U.S. Pat. No. 5,498,392; WO 91/16966; WO 92/13967; F 90 09894, as well as the publications of S. Poser, T. Schulz, U. Dillner, V. Baier, J. M. Koehler, D. Schimkat, G. Mayer, A. Siebert (Chip elements for fast thermocycling, Sensors and Actuators A, 1997: 62 672-675) and M. U. Kopp, A. J. de Mello, A. Manz (Chemical amplification: Continuous-flow PCR on a chip, Science, 1998: 280 1046-1048) various miniaturizable or miniaturized methods and devices (thermocycler) for performing PCR are known.

In the documents DE 195 19 015 A1; WO 94/05414; U.S. Pat. No. 5,587,128; U.S. Pat. No. 5,498,392 and the publication of S. Poser, T. Schulz, U. Dillner, V. Baier, J. M. Koehler, D. Schimkat, G. Mayer, A. Siebert (Chip elements for fast thermocycling, Sensors and Actuators A, 1997: 62 672-675) thermocycler are described consisting of capped chambers that receive the samples.

The miniaturizable or miniaturized thermocyclers presented in the documents U.S. Pat. No. 5,716,842; DE 195 19 015 A1; WO 91/16966; WO 92/13967; F 90 09894, and in the publication of M. U. Kopp, A. J. de Mello, A. Manz (Chemical amplification: Continuous-flow PCR on a chip, Science, 1998: 280 1046-1048) work on the principle of liquid sample being pumped continuously across three temperature zones.

The disadvantage of all of these above-mentioned solutions is that in an online detection only the information can be obtained whether nucleic acid has been amplified, or if possible, how much nucleic acid has been amplified. A characterization of the amplification products is not possible beyond that.

In the document U.S. Pat. No. 5,856,174, a system is disclosed by means of which it is possible to pump liquid samples to and from e.g. three miniaturized chambers. In one chamber of said system ensues PCR, in the next, a reprocessing reaction is realized, and in the third, reaction products are detected, e.g. by means of a DNA chip. The PCR chamber in question is a standard vessel such as it is well described in the literature (S. Poser, T. Schulz, U. Dillner, V. Baier, J. M. Koehler, D. Schimkat, G. Mayer, A. Siebert, Chip elements for fast thermocycling, Sensors and Actuators A, 1997: 62 672-675). The disadvantage of this system consists in that a complicated, failure-prone and control technically expensive system of pressure-driven fluidics has to be built up for conveying the liquid sample from the PCR chamber to the detection chamber. Moreover, the separation of amplification and detection leads to an extension of the total time of the analysis.

The genetic characterizations, e.g. for the identification and taxonomic classification of microorganisms, at present ensue by means of DNA-DNA hybridization studies, rRNA gene sequence comparisons (e.g. by means of the 16S or 23S rRNA gene sections) subsequent to carrying out sequentialization of these sections, as well as by means of restriction fragment length polymorphism examinations (RFLP) or PCR examinations with specific primers by means of gel-electrophoretic segregation and detection of the restriction products or PCR products (T. A. Brown, 1996, *Gentechnologie für Einsteiger*, Spektrum Akademischer Verlag Heidelberg, Berlin, Oxford).

The known RFLP examinations are based on an individual-specific distribution of endonuclease restriction interfaces, which relates to DNA sequence differences in the sphere of genome DNA that has a high-grade homology to a marked DNA probe used for the hybridization (T. A. Brown, 1996, *Gentechnologie für Einsteiger*, Spektrum Akademischer Verlag Heidelberg, Berlin Oxford).

The RFLP examination, which, for example, is used in the HLA diagnostics (Humane Leukocyte Antigen) in immunology in the preliminary stage of transplantations or transfusions (cf. Cesbron A., Moreau P., Milpied N., Muller J Y., Harousseau J L., Bignon J D., "Influence of HLA-DP mismatches on primary MLR responses in unrelated HLA-A, B, DR, DQ, Dw identical pairs in allogeneic bone marrow transplantation" Bone Marrow Transplant 1990, Nov. 6: 5, 337-40 or Martell R W., Oudshoom M., May R M., du Toit E D., "Restriction fragment length polymorphism of HLA-DRw53 detected in South African blacks and individuals of mixed ancestry" Hum. Immunol. 1989, Dec. 26: 4, 237-44) embraces the isolation of genomic DNA, the splitting of the restriction endonuclease of the DNA, a fractionation of the DNA fragments, a transfer and an immobilization of the DNA fragments, the preparation and marking of hybridization probes, the hybridization, the detection, as well as the correlation and interpretation. The disadvantage of this examination, which could not be automated to date, is that such an analysis is very laborious and time-consuming (it runs from 5 to 10 working days), and has a low sample throughput (one employee typifies only up to 50 samples in parallel), so that it is very cost-intensive.

The characterization of genome sections, which can be conducted with DNA molecules or ribonucleic acid molecules (RNA molecules) by hybridization with specific gene probes (Leitch, A. R., Schwarzacher, T., Jackson, D., and Leitch I. J., 1994, *In-situ Hybridisierung*, Spektrum Akademischer Verlag Heidelberg, Berlin, Oxford), has been carried out routinely for several years. Gene probes are single-stranded nucleic acid molecules of a known nucleotide base sequence of an optimum length of 100 to 300 bases, which lead to a double-stranded nucleic acid pairing specifically with single-stranded nucleic acid sections, e.g. of one gene, and are in most cases provided with a non-radioactive or radioactive reporter element (marker), e.g. a fluorescing pigment or radionucleotides that serve for detecting the gene probes. A differentiation is made between double-stranded DNA probes, single-stranded RNA probes, tailor-made synthetic oligonucleotide probes having a length of 10 to 50 bases, genome probes and DNA probes produced by PCR (Leitch, A. R., Schwarzacher, T., Jackson, D., and Leitch I. J., 1994, *In-situ Hybridisierung*, Spektrum Akademischer Verlag Heidelberg, Berlin, Oxford).

With the hybridization, a differentiation is made between the hybridization of probes with an isolated single-stranded nucleic acid (DNA or RNA) and the so-called in-situ hybridization (on-site hybridization in tissues, cells, cell nuclei and chromosomes), wherein the gene probe couples to a spreaded (single-stranded) nucleic acid (DNA or RNA) Leitch, A. R., Schwarzacher, T., Jackson, D., and Leitch I. J., 1994, *In-situ Hybridisierung*, Spektrum Akademischer Verlag Heidelberg, Berlin, Oxford). It is particularly important with this in-situ hybridization that the target sequence and the tissue morphology remains maintained, and that the preserved tissue is permeable for the probe and the analytical reagents. This permeability is not always given, a fact constituting a disadvantage of this method.

The hybridization of probes with isolated and spread chromosomes, which is likewise designated as in-situ hybridization, avoids the disadvantage of the permeability barrier, since the chromosomes are present freely accessible for the probes, e.g. fixed on a carrier. (T. A. Brown, 1996, *Gentechnologie für Einsteiger*, Spektrum Akademischer Verlag Heidelberg, Berlin, Oxford).

The presence of single-stranded nucleic acid target molecules and nucleic acid probe molecules is essential for the hybridization, which is in most cases effected by thermal denaturation, as well as the selected optimum stringency (setting of the parameters: temperature, ionic strength, concentration of helix-destabilized molecules), which guarantees that only probes having almost perfectly complementary sequences (corresponding to one another) remain paired with the target sequence (Leitch, A. R., Schwarzacher, T., Jackson, D., and Leitch I. J., 1994, *In-situ Hybridisierung*, Spektrum Akademischer Verlag Heidelberg, Berlin, Oxford).

Classical applications of the probe technology enabling the identification of unknown organisms or the detection of determined organisms in a mixture of organisms, are, for example, phylogenetic studies or the detection of microbes in medical diagnostics. The detection of the organisms is often based in both fields on the analysis of the genes for ribosomal RNA (rRNA, rDNA), which are particularly suited for this purpose due to their ubiquitous distribution and the existence of variable, species-specific sequence sections. Apart from these qualities, rDNA contains flanking sequence sections, which are highly conserved within the realm of the respective organism. Primer sequences directed against these sections can be used for a species-independent amplification of the rDNA (G. Van Camp, S. Chapelle, R. De Wachter, Amplification and Sequencing of Variable Regions in Bacterial 23S Ribosomal RNA Genes with conserved Primer Sequences. Current Microbiology, 1993, 27: 147-151, and W. G. Weisburg, S. M. Barns, D. A. Pelletier, D. J. Lane; 16S ribosomal DNA Amplification for Phylogenetic studies, J. Bacteriol, 1991, 173: 697-703), whereby the sensitivity of subsequent detection methods is considerably increased.

In dependence of the specific setting of targets, various established methods for the rDNA-supported identification of organisms are available.

For the identification of unknown organisms, the entire (mostly 16S) rDNA, as a rule, is amplified with two universal primers per PCR, and is subsequently sequenced. In this way, extensive rDNA databases have developed containing at present sequences of several thousands of organisms (e.g. RDP/Ribosomal Database Project II, Michigan State University,) allowing the phytogenetic assignment of new sequences. This method, in principle, allows the detection of any arbitrary organism, but is very time-consuming and therefore inappropriate for diagnostic applications. Moreover, the process is affected by a series of error sources (F. Wintzingerrode, U. B. Goebel, E. Stackebrand; Determination of microbial diversity in environmental samples: pitfalls of PCR-based rRNA analysis. FEMS Microbiology Reviews, 1997, 21: 213-229), whereby, in particular, recombination processes and point mutation lead to false results during the PCR amplification.

A series of alternative techniques have been developed for diagnostic applications. Mattsson and Johansson (J. G. Mattsson, K. E. Johansson; Oligonucleotide probes complementary to 16S rRNA for rapid detection of mycoplasma contamination in cell cultures. FEMS Microbiol. Lett., 1993: 107 139-144) describe a method, in which ribosomal RNA is isolated from mycoplasmas, immobilized on filters, and identified by hybridization of three different specific oligonucleotides. This method is relatively fast, the number of the organisms to be identified and the sensitivity of the identification, however, are limited.

McCabe et al. (K. M. McCabe, Y. H. Zhang, B. L. Huang, E. A. Wagar, E. McCabe, Bacterial species identification after DNA amplification with a universal Primer pair. Mol. Gen. Metab., 1999; 66: 205-211) describe a method in which rDNA of clinical bacterial isolates lysated on filter spots is amplified using universal primers, and is subsequently identified by hybridization with specific probes. This method is sensitive; the number of the species to be identified, however, is likewise limited.

In a method used by Oyarzabal et al. (O. A. Oyarzabal, I. V. Wesley, K. M. Harmon, L. Schroeder-Tucker, J. M. Barbaree, L. H. Lauerman, S. Backert, D. E. Conner; Specific identification of *Campylobacter* fetus by PCR targeting variable regions of the 16S rDNA. Vet. Microbiol., 1997, 58: 61-71), in which 16S rDNA of a *campylobacter* species is identified by means of specific probes and the size of the product determined, only a yes/no answer can be generated for a single specific microbe.

The invention is based on the problem of providing a device allowing for an almost simultaneous duplication and characterization of nucleic acids with a high sample throughput rate, and hence avoiding the prior art disadvantages. This and other problems of the present invention resulting in the following from the description, are solved by the characterizing features of the independent claim. Advantageous embodiments are covered by the depending claims.

The problem is thereby inventively solved in that a device is provided which is characterized in that a chamber body containing an optically permeable chip having a detection area, and being optically permeable at least in the zone of the detection area of the chip, is sealingly placed on an optically permeable chamber support, so that a sample chamber having a capillary gap is formed between the chamber support and the detection surface of the chip, which is temperature-adjustable and flow-controllable. This type of constructions allows reactions to be carried out, which efficiently take place only in determined temperature ranges, and to detect almost simultaneously the reaction products by chip-based experiments.

An inventive device can, for example, be used so as to duplicate nucleic acid molecules by PCR and to almost simultaneously identify the PCR products by chip-based experiments. By the fact that the liquid sample of such a reaction is present in the capillary gap, it can be efficiently heated and cooled by corresponding temperature adjustment means.

The inventive device can likewise be used for carrying out a reverse transcription reaction and for transforming in that way, for example, mRNA into cDNA, and for characterizing the reaction products by hybridization on the chip. Thus, a so-called "gene profiling" can be carried out. Since the reverse transcription, as well as the hybridization are carried out in one chamber, the method is extremely time-efficient and scarcely failure-susceptible.

By means of an inventive device, a digestive restriction process at desired temperatures can, for example, likewise be carried out in the reaction chamber, and the reaction products can be characterized by hybridization on a chip. The denaturization of the enzymes can ensue by means of heat deactivation. Therewith, the inventive device enables a time-efficient restriction fragment length polymorphism mapping.

By means of the device, a ligation can, for example, be realized, as well.

The inventive devices can also be used for performing tests as to the bonding behaviour of proteins in dependence of the temperature. It can, for example, be tested in this way whether antibodies are still capable of binding their antigens subsequent to heating over a prolonged period of time. A prerequisite for this is, that in this case, the chip is not functionalized by nucleic acid molecules but by the corresponding proteins.

An inventive device thereby allows, in general, an almost simultaneous, time-efficient and scarcely failure-susceptible reprocessing and/or conditioning reactions and the chip-based characterization of the reaction products to be performed. By the term reprocessing reaction and/or conditioning reaction according to the invention, a reaction is thereby understood, the reaction products of which can be characterized by chip-based tests.

An advantage of the inventive device consists in that by means of the device, the PCR and the hybridization parallel to chip-bound nucleic acid are spatially combined in a temperature-controllable and throughput-controllable cell (chamber). The chamber thereby holds in its interior a chip, which generates between the chamber bottom and the detection surface of the chip, a capillary gap receiving the liquid sample, the thorough mixing of the liquid sample ensuing by an induced electro-osmotic flow.

In an advantageous embodiment, the chamber forms a gas reservoir around the capillary gap and the chip, through which gas reservoir, a gas reservoir nose leads to the capillary gap and separates an inlet from an outlet so that the samples can be injected through the inlet, arrive in the capillary gap due to the capillary forces, and can be discharged from there through the outlet. With a filled capillary gap, due to surface tension effects, an air gap is generated as a ring around the chip located in the chamber and around the capillary gap (serving as a sample reservoir), so that the chip and the capillary gap are thermally insulated from the chamber body, a fact allowing for the probes being rapidly heated and cooled down by heating and cooling elements, which are placed on a chamber support together with temperature sensors and electrodes, which chamber support holding the chamber and being in a heat-conducting contact with same through the chamber bottom. By the fact that the capillary gap serves as a sample reservoir, the evaporation rate of the liquid sample is highly reduced even at temperatures close to the boiling point, since the sample can only evaporate through the edge of the capillary gap.

The capillary gap (the sample reservoir) is the place of the nucleic acid amplification in the liquid sample by PCR with specific primers, as well as of the genetic characterization of the sample. The marked PCR products are thereby fished from the liquid probe by the immobilized specific probes which are bound on the nucleic acid chip. The chamber and the chip are optically transparent, and enable, due to their configuration, the online detection of the marking signal of the PCR products bound to the probes.

As compared to the methods used to date, the inventive device has the advantage that in a minimum of diagnosis time with a minimum of sample volumes, a maximum of genetic typification using specific probes is possible within a temperature-controllable and throughput-controllable cell in an automated manner and at a high sample throughput rate, whereby through PCR, an accentuation of diagnostically relevant gene structures as compared to a sequence background, and through the almost simultaneous, parallel hybridization of the PCR products to the chip-bound nucleic acid, a specific detection being caused.

The inventive device is, for example, used for the simultaneous identification of various microbial pathogens (e.g. on the basis of the 16S or 23S rRNA analysis), the screening for resistances of individual pathogenic microorganisms or a genomic typification of diagnostically relevant allele structures of eukaryote cells, the parallel identification being enabled by the chip with its various probes specific for the different target sequences.

BRIEF DESCRIPTION OF THE DRAWINGS

The invention will be described hereinafter in more detail by means of the schematic drawings and the application examples. Therein shows:

FIG. 1, FIG. 3: a top view of the device as per FIG. 1, FIG. 4: a schematic representation of the lower side view of the device as per FIG. 1, FIG. 5: a cross-section along plane B-B as per FIG. 4, FIG. 6: a schematic representation of the top view of the chamber support of the device as per FIG. 1, FIG. 7: a cross-section along plane C-C as per FIG. 6, FIG. 8: a schematic representation of a possible quadrupole arrangement on the chamber support of the device as per FIG. 1, FIG. 9: a cross-section along plane D-D as per FIG. 8, FIG. 10*a*: a schematic representation of a possible positioning of a liquid sample within the device as per FIG. 1, FIG. 10*b*: a cross-section along plane E-E as per FIG. 10*a*, FIG. 11: a schematic block diagram of a possible integration of the device as per FIG. 1 into an assay system, FIG. 1, FIG. 14: a schematic representation of an embodiment of a chip of the device as per FIG. 1, and FIG. 15: a schematic representation of secondary and tertiary amplification products of the chip as per FIG. 14.

Figure 1:
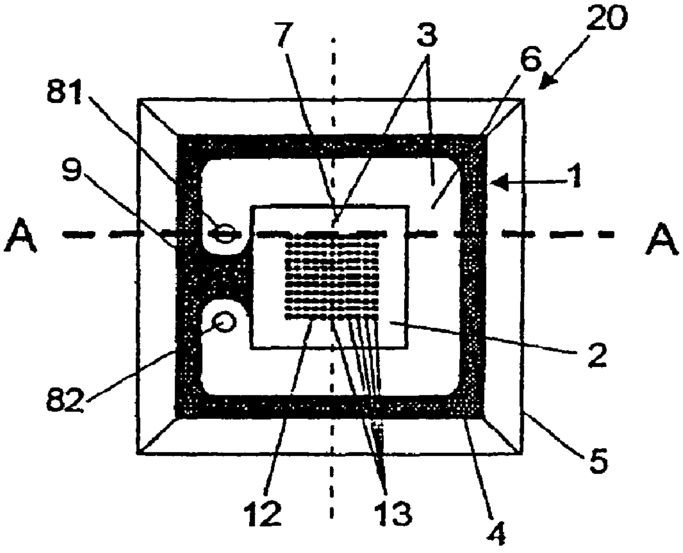
FIG. 1: a principle representation of a possible embodiment of an inventive device for duplicating and characterizing nucleic acids.
Figure 2:
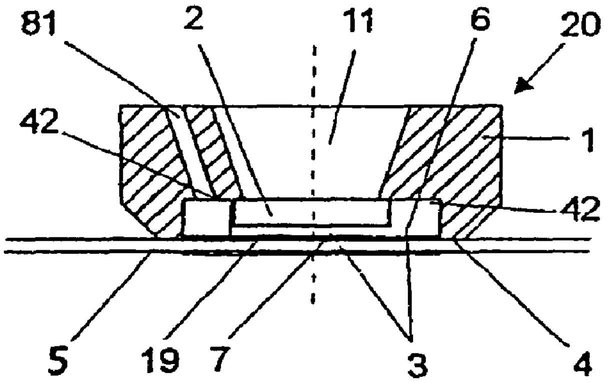
FIG. 2: a cross-section along plane A-A as per

Device 20 shown in FIG. 1 for duplicating and characterizing nucleic acids, consists of a chamber body 1 and a chamber support 5. Chamber body 1 is provided with a bearing surface 4, via which chamber body 1 is in a sealing connection with chamber support 5, so that a sample chamber 3 is formed. Said sample chamber 3 consists of a gas reservoir 6, as well as of a capillary gap 7, and is provided with at least one inlet 81 and at least one outlet 82. Inlet 81 and outlet 82 lead into sample chamber 3, and are spaced from an interposed gas reservoir nose 9 of gas reservoir 6. Chamber body 1, which, for example, is in an unreleasable sealing connection with a chamber support 5 by means of an adhesive connection or weld connection not shown in detail, holds a chip 2, e.g. a nucleic acid chip. Said chip 2 carrying detection surfaces 12 in the form of spots 13, is mounted in the chamber body 1 in such a way that the detection surfaces 12 in the form of spots are positioned opposite and facing the surface of the chamber support 5, and are uniformly spaced from the chamber support 5 by edge 42 of chamber support 5, so that chip 2 and chamber support 5, such as it is shown in FIG. 2, generate capillary gap 7, which serves as a sample reservoir. Said capillary gap 7 receives liquid sample 19.

Chamber body 1 preferably consists of materials such as glass and/or synthetic material. Synthetic materials suitable for injection-molding can be used for its fabrication. Inter alia, synthetic materials such as nylon, PMMA and Teflon can be used. In a preferred embodiment, the chamber body is made of optically permeable materials such as glass, PMMA, polycarbonate, polystyrene and topaz. The selection of the materials thereby is to be adapted to the application purpose of the device. If the device, is for example, intended for being used for the performance of a PCR, then only those synthetic materials may be used, which are stable at temperatures such as 95° C. over prolonged periods of time.

Chamber body 1 consists, for example, of an optically transparent synthetic material or glass, whereby sample chamber 3 representing a space for filling in liquid sample 19, can be realized by a milling operation, and inlet 81, as well as outlet 82, which represent guiding paths for the liquid sample, can be realized in the chamber body 1 by a boring operation.

The chip can preferably be made of borofloat glasses, of quartz glass, a monocrystalline $CaF_2$, of sapphire plates, of topaz, PMMA, polycarbonate and/or polystyrene. The selection of the materials thereby has to be conformed to the subsequent application purpose of the device and the chip, respectively. If the chip is, for example, used for characterizing PCR products, only those materials may be used, which are capable of withstanding a temperature of 95° C. The chips are preferably functionalized by nucleic acid molecules, in particular by DNA or RNA molecules. However, they can likewise be functionalized by peptides and/or proteins such as, for example, antibodies, receptor molecules, pharmaceutically active peptides and/or hormones.

Nucleic acid chip 2 consists in a known manner of an optically transparent support, the material of which, for example, can be silicon or glass, or of nucleic acid molecules of a specific sequence (e.g. probes) immobilized on said support.

Sample chamber 3 comprises gas reservoir 6 and capillary gap 7, whereby gas and air bubbles collect in gas reservoir 6 upon filling in of the liquid sample 19 due to surface tension effects, so that chip 2 and capillary gap 7 are thermally insulated from chamber body 1. Capillary gap 7 forming the sample reservoir (e.g. with a volume of 1.8 μl), ensures that detection surface 12 is completely moistened by liquid sample 19.

Inlet 81 and outlet 82 serve for guiding liquid probe 19, whereby a filling and emptying of sample chamber 3, and hence, a filling and emptying of capillary gap 7 is possible, as well, due to the influence of the capillary forces.

Inlet 81 and outlet 82, which, for example, can run adjacent to one another such as it is shown in FIG. 1, are spatially separate from each other through a gas reservoir nose 9, so that liquid sample 19 is prevented from flowing from inlet 81 to outlet 82 without entering capillary gap 7.

Chamber support 5 preferably consists of glass, synthetic materials and/or ceramic materials. The chamber support can, for example, be made of aluminum oxide ceramics, of nylon and/or Teflon. Chamber support 5 preferably consists of optically permeable materials such as glass and/or optically permeable synthetic materials. The chamber support can, for example, be made of PMMA, polycarbonate and/or polystyrene. The selection of the materials thereby is to be adapted to the application of the device. The temperatures, for example, to which the device will exposed, is to be taken into account with the selection of the materials. Chamber body 5 can be connected with heating elements 17, and should thereby consist of materials of a good thermal conductivity.

Figure 4:
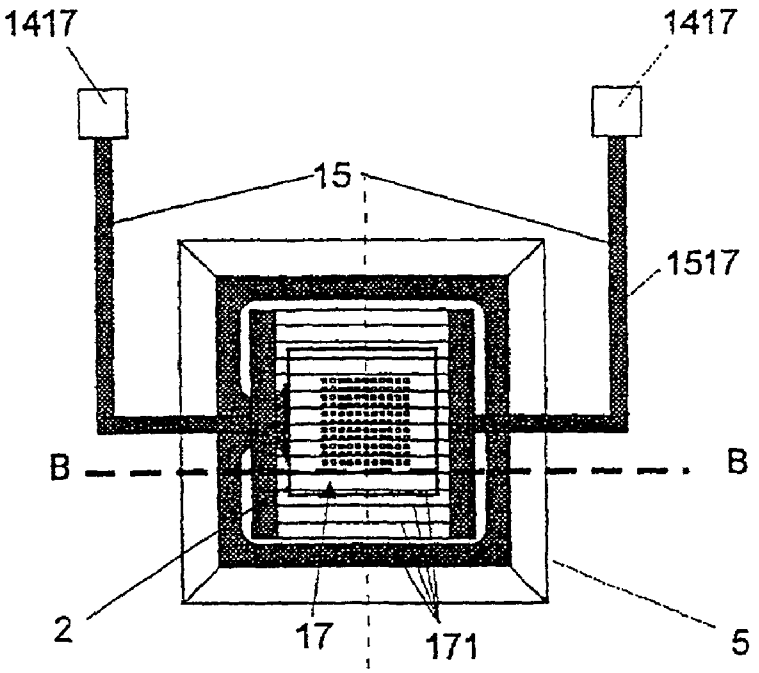
Figure 6:
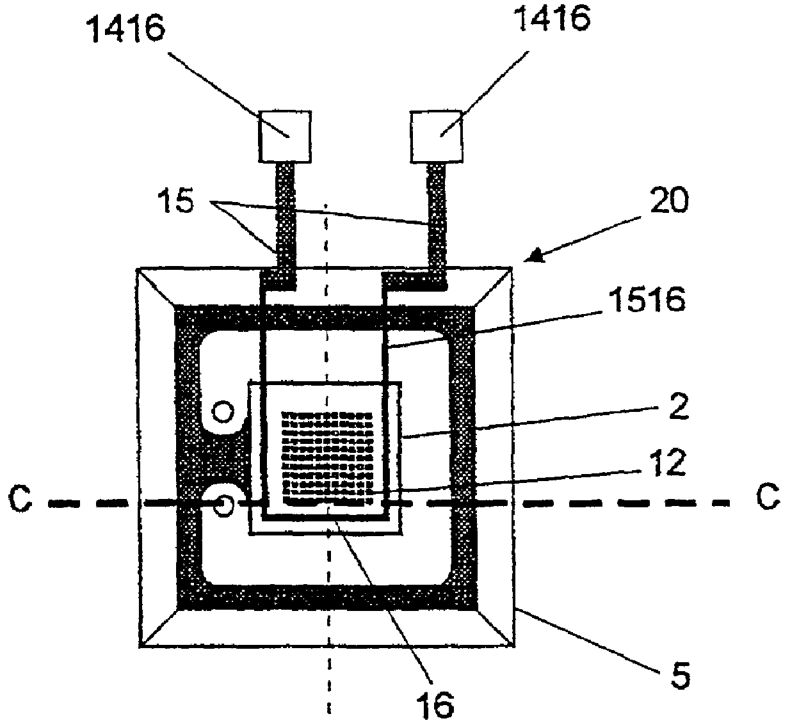
Figure 8:
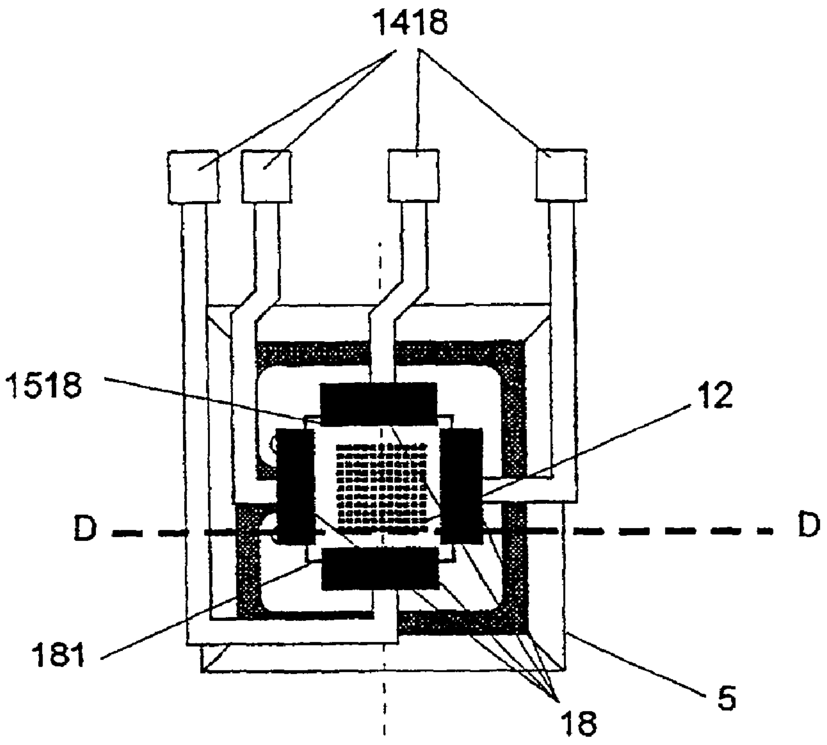

Chamber support 5, which is optically transparent and of a good heat conductivity, e.g. consists of glass, and is provided such as it is shown in FIGS. 4, 6 and 8 with heating elements 17, e.g. in the form of miniaturized heaters or miniaturized temperature sensors 16, as well as with electrodes of a quadrupole 18, so that it is possible to temper liquid sample 19 and to thoroughly mix liquid sample 19 by means of an induced electro-osmotic flow. In another embodiment of device 20 not shown in detail, chamber body 1 can be provided with the heating elements 17 and the miniaturized temperature sensors 16, as well as with the electrodes of quadrupole 18.

The heating elements 17 can be preferably selected so that a fast heating and cooling of the liquid in the capillary gap is possible. The term fast heating and cooling is thereby so understood that by means of the heating elements, temperature changes in a temperature range from 0.5° K/s to 10° K/s can be imparted. Preferably, temperature changes from 1° K/s to 10° K/s can be imparted by the heating elements 17.

The temperature sensors 16 can, for example, be realized as resistance temperature sensors of a nickel chromium thick film. The length of the temperature sensors 16 is, for example 10.4 mm in the event that chamber support 1 has a surface area of 8×8 mm, and chip 2 has a surface area of 3×3 mm or less, and the width of temperature sensor 16 is in this example 50 μm, so that the resistance at 20° C. is 4 kOhm, and the temperature coefficient $TK_R$ at 0° C. is 1500 ppm. Alternatively thereto, the temperature sensors 16 can likewise be realized as optically transparent thin films.

Heating elements 17 can, for example, be realized as resistance heaters of nickel chromium thick film. With the dimensions of the preceding example, heating elements 17 have a length of 2.6 mm, and a width of eight single tracks each of a width of 50 μm, so that the resistance at 20° C. is 300 Ohm. Alternatively thereto, heating elements 17 can likewise be realized as optically transparent thin films.

Quadrupole 18 can, for example, be realized as gold titanium electrodes. With the dimensions of the preceding example, these electrodes have a length of 2.2 mm and a width of 0.5 mm. The quadrupole serves for inducing an electro-osmotic flow, a fact which leads to a thorough mixing of liquid sample 19 in sample chamber 1. Alternatively thereto, quadrupole 18 can likewise be realized as an optically transparent thin film.

FIG. 2 shows chamber body 1 in a rigid, unreleasable connection with chamber support 5 through its bearing surface 4. This connection, for example, can be realized by adhesion. Alternatively thereto, for example, exists also the possibility of connecting chamber support 5 and chamber body 1 with one another by a melt connection or by manufacturing same integrally. Between chamber support 5 and the clip 2 held by chamber body 1 through the edge 42 thereof, capillary gap 7 (serving as a sample reservoir) is located, which due to its capillary action is capable of taking up liquid sample from sample chamber 3.

Across sample chamber 1, inlet 81 and outlet 82 lead into gas reservoir 6 of sample chamber 3, so that liquid sample 19 can be filled in through gas reservoir 6 into capillary gap 7, and can be discharged through outlet 82. Alike chamber body 1, chip 2 is made of an optically transparent or diaphanous material such as glass, so that optical and photometrical evaluations, such as fluorescence measurements of the detection surface 12 through a conical opening in chamber body 1, namely recess 11 building a straight visual cone, are possible.

Figure 3:
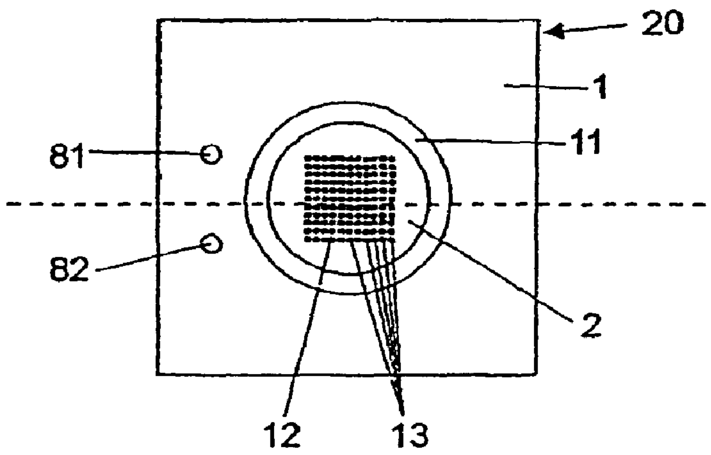

FIG. 3 shows inlet 81 and outlet 82, as well as recess 11, across which detection surface 12 including spots 13 of chip 2 are optically accessible. This optical accessibility enables the above-mentioned optical and photometrical evaluations of the signals coming from detection surface 12, in the example the fluorescence signals, which are not illustrated.

In FIG. 4, the heating elements 17 situated at the lower side of the transparent chamber support 5 including conducting paths 1517 and connecting surfaces 1417 are shown. The heating elements 17 of the example consist of eight individual micro-structured resistance heating conductors 171 connected in parallel, through which chamber support 5 situated below chamber body 1, and together with same, liquid sample 19 filled into capillary gap 7 can be heated homogenously. Resistance conductors 171 of heating elements 17, which can be acted upon with a variable, definably pre-settable temperature, have such dimensions that the above-mentioned optical accessibility of detection surfaces 12 of chip 2 is guaranteed.

Figure 5:
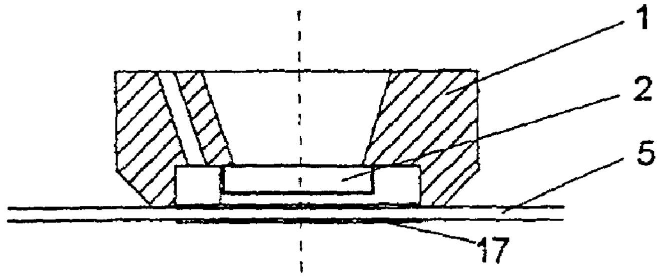

FIG. 5 shows the positioning of heating elements 17 at the side of chamber support 5 facing away from chamber body 1. Said chamber support 5 carries chamber body 1 including supported chip 2.

In FIG. 6, a temperature sensor 16 including conductive paths 1516 and connecting surfaces 1416 is shown mounted on the upper side of the transparent chamber support 5. Temperature sensor 16 is thereby mounted around detection surface of chip 2, so that the mentioned optical accessibility of detection surface 12 is guaranteed. Temperature sensor 16 is electrically insulated with respect to elements arranged downstream of device 20 and to liquid sample 19 by a passivation layer not shown in the illustration.

Figure 7:
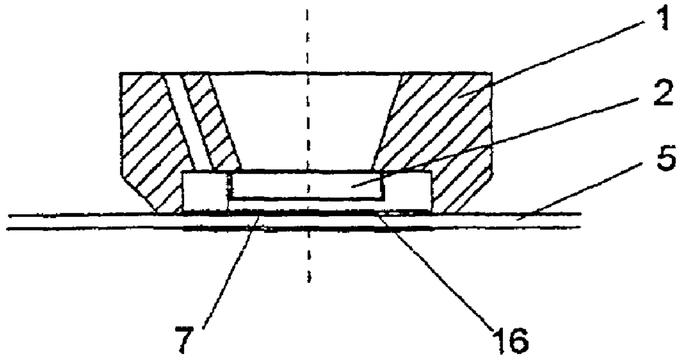

FIG. 7 shows the positioning of temperature sensor 16 at the surface side of chamber support 5 facing chamber body 1, which side at the same time being the surface side of chamber support 5, by means of which chip 2 supported by chamber body 1 generates capillary gap 7.

FIG. 8 shows a quadrupole 18 applied on the passivation layer not shown in detail of temperature sensor 16, including the associated conductive paths 1518 and connecting surface 1418. Quadrupole 18 is in electrically conducting contact with liquid sample 19, so that by alternately applying voltage of +1 V to two electrodes 181 of quadrupole 18, a swirl induced by the electro-osmotic flow can be provoked in capillary gap 7 filled with liquid sample 19. If voltage is applied to another pair of electrodes 181 of quadrupole 18, then the swirl conditions will change. By continuously alternating the pairs of electrodes 181 which are charged, an efficient mixing of liquid sample 19 takes place. By an applied low voltage of just one volt, it is prevented that liquid sample 19 in capillary gap 7 is subjected to electrochemical modifications and gas bubbles, for example, are prevented from forming. As shown in this Figure, quadrupole 18 thereby is so configured that the optical accessibility of detection surface 12 is guaranteed. Alternatively thereto, quadrupole 18 can likewise be realized as an optically transparent thin layer.

Figure 9:
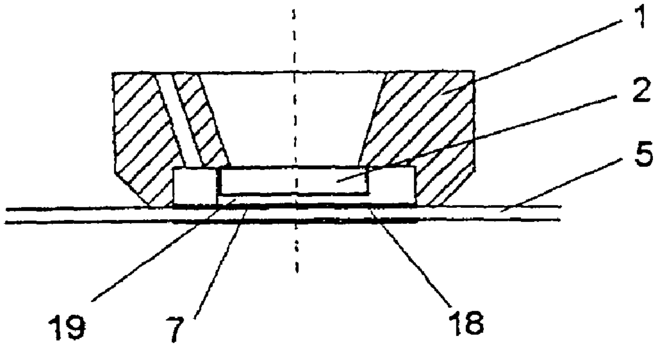

FIG. 9 shows the positioning of quadrupole 18 at the surface side of chamber support 5 facing chamber body 1.

Figure 10A:
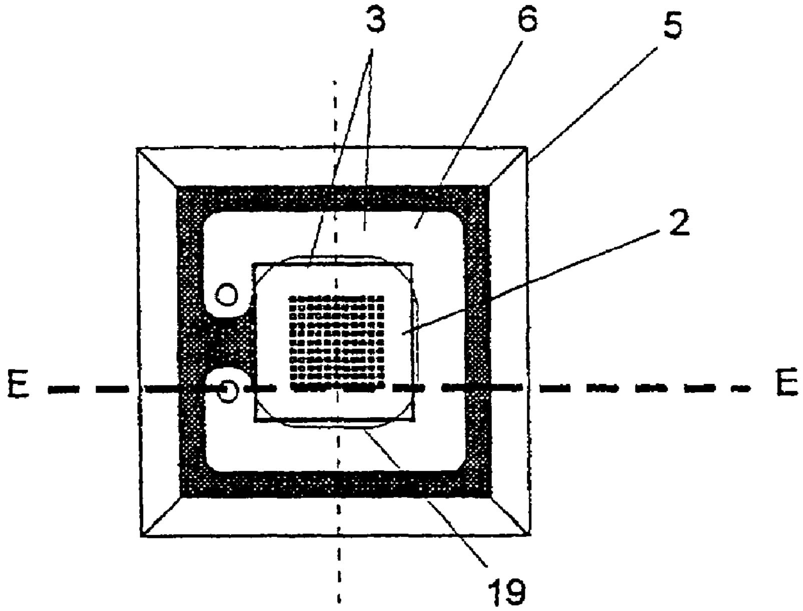
Figure 10B:
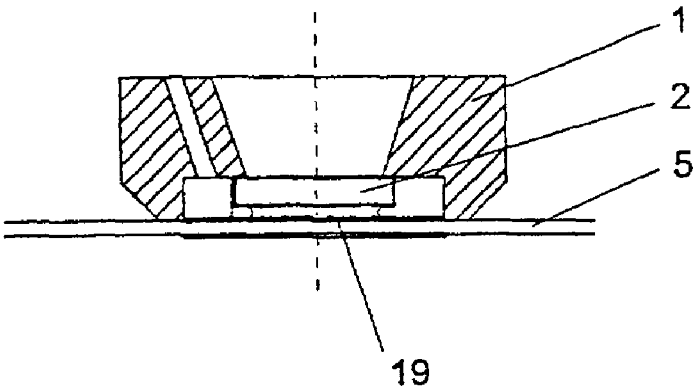

FIGS. 10*a* and 10*b* schematically show liquid sample 19 stored in capillary gap 7, chamber body 1 and chamber support 5 by capillary forces.

Due to the size of gas reservoir 6, contingent air bubbles not shown in detail, can be discharged from capillary gap 7 into gas reservoir 6 of sample chamber 3, driven by the minimization of the interfacial energy. Thereby, an air ring forms around liquid sample 19, thermally insulating same and chip 2 from chamber body 1, so that liquid sample 19 in capillary gap 7 can be rapidly heated up and cooled down at a low energy consumption. Thereby, the evaporation rate of liquid sample 19 is strongly reduced even at temperatures close to the boiling point, since liquid sample 19 can only evaporate over the edge of capillary gap 7. In addition, the quantity required of liquid sample 19 in the sample reservoir 7 is low (in the μl range), since capillary gap 7 only constitutes a minor space volume, whereby the required sample volumes are very small.

Due to the described good thermal insulation of chip 2 and liquid sample 19 with respect to chamber body 1, as well as the low volume of liquid sample 19, the heating and cooling rates usual for micro-thermocyclers described by Posner et al. may be obtained (S. Poser, T. Schulz, U. Dillner, V. Baier, J. M. Koehler, D. Schimkat, G. Mayer, A. Siebert; Chip elements for fast thermocycling, Sensors and Actuators A 1997, 62: 672-675). At the same time, the temperature homogeneity of liquid sample 19 and the heat input into liquid sample 19, which is positioned in capillary gap 7 between chip 2 and temperature-controllable chamber support 5, is guaranteed to a high extent due to the important ratio of heating surface to sample volume.

Figure 11:
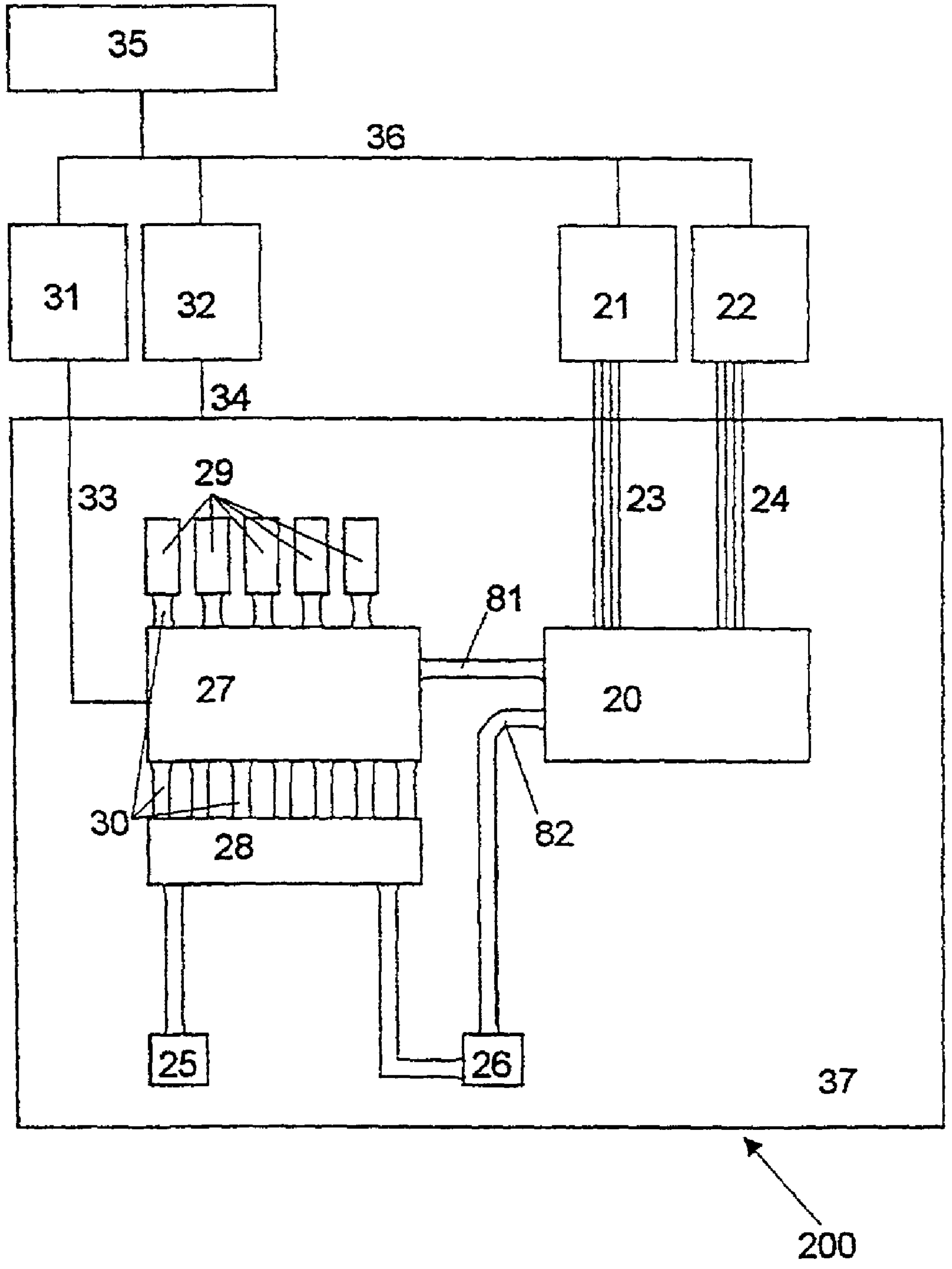

FIG. 11 shows the installation of device 20 for duplicating and characterizing nucleic acids in an assay system 200. Assay system 200 thereby consists of a temperature controller 21, a mixing control 22, electric lines 23, 24, 33, 34, an overall inlet 25, a waste receptacle 26, a conditioner 27, valves/pumps 28, storage tanks 29, connecting tubes 30, a conditioner control 31, an automat control 32, a control computer 35, a computer bus 36, and a pipetting automat 37. Device 20 is in direct communication with conditioner 27 and the waste receptacle 26 through inlet 81 and outlet 82, and with temperature controller 21 and mixing control 22 through the electric lines 23 and 24, the temperature controller being coupled with temperature sensors 16 and heating elements 17 and mixing control being coupled with quadrupole 18.

In device 20 for duplicating and characterizing nucleic acids, which is integrated in assay system 200, liquid sample 19 can be pipetted into overall inlet 25 from microplates not shown in detail through pipetting automat 38. By means of valves and pumps 28, which are in liquid-conducting communication with overall inlet 25, liquid sample 19 can be guided into conditioner 27 through connecting tubes 30, conditioner 27 serving for reprocessing liquid sample 19 (e.g. setting of the pH value and filtering out of interfering elements). The buffer liquids and reaction solutions for this reprocessing can be imported from storage tanks 29, which are in a liquid-conducting communication with conditioner 27. Pipetting automat 37 and conditioner 27 are in communication with conditioner control 31 and automat control 32 through the electric lines 33, and serve for the control of same. Inlet 81 and outlet 82 of chamber body 1, which lead into gas reservoir 6, serve for conducting liquid from conditioner 27 through capillary gap 7 to waste receptacle 26.

In device 20, liquid sample 19 can be temperature-controlled and mixed by means of temperature controller 21 and mixing control 22 in the zone of capillary gap 7. Capillary gap 7 therefore is the place of the amplification and characterization of a nucleic acid in the example of the target DNA.

Figure 12A:
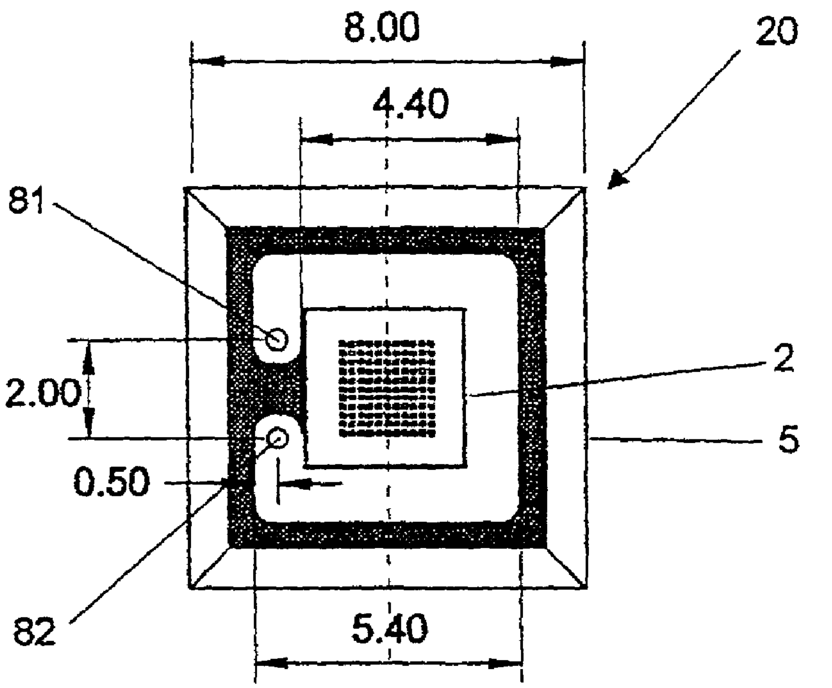
FIG. 12*a*: an indication of the dimensions of a device as per FIG. 1, in millimeters.
Figure 12B:
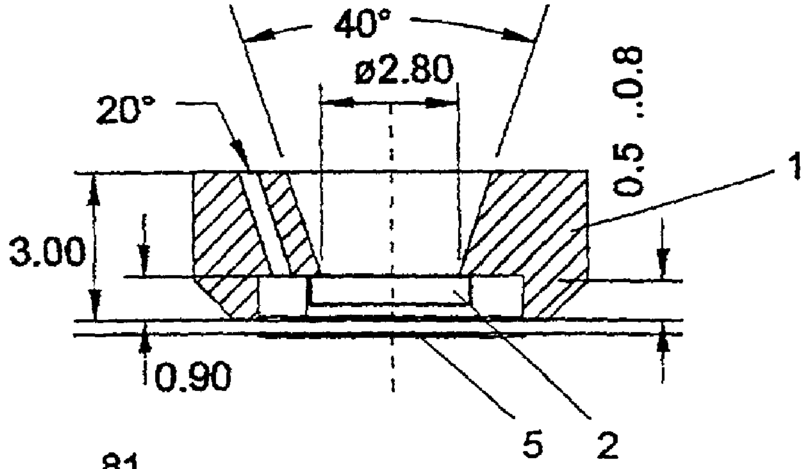
FIG. 12*b*: an indication of the dimensions of a device as per FIG. 2, in millimeters.
Figure 12C:
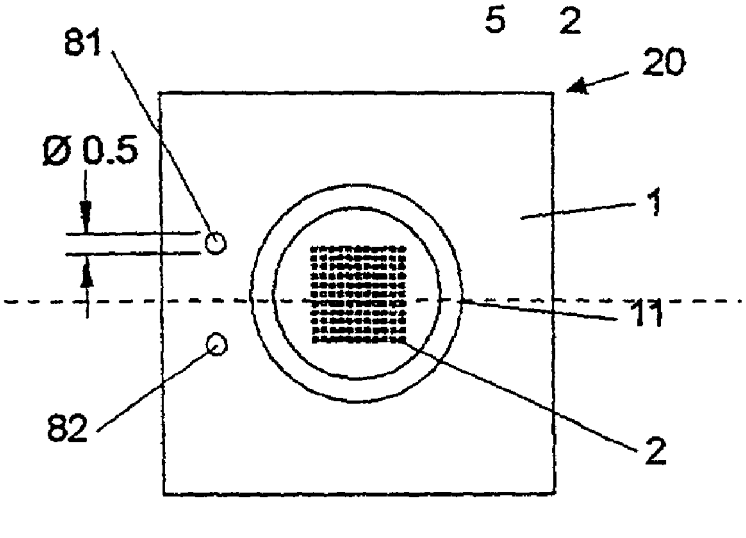
FIG. 12*c*: an indication of the dimensions of a device as per FIG. 3, in millimeters.

FIGS. 12*a* through *c* show in an example of an embodiment of device 20 that chamber body 1 has a length and a width of 8 mm, and a height of 3 mm, that the gas reservoir has a length and a width of 5.4 mm and a height of 0.5 to 0.8 mm, chamber support 5 has a thickness of 0.9 mm, recess 11, on its side facing chip 2, has a diameter of 2.8 mm, and inlet 81 and inlet 82 have a diameter of 0.5 mm, inlet 81 and outlet 82, as well as recess 11 featuring an inclination of 70 degrees with respect to chamber support 5.

Figure 13:
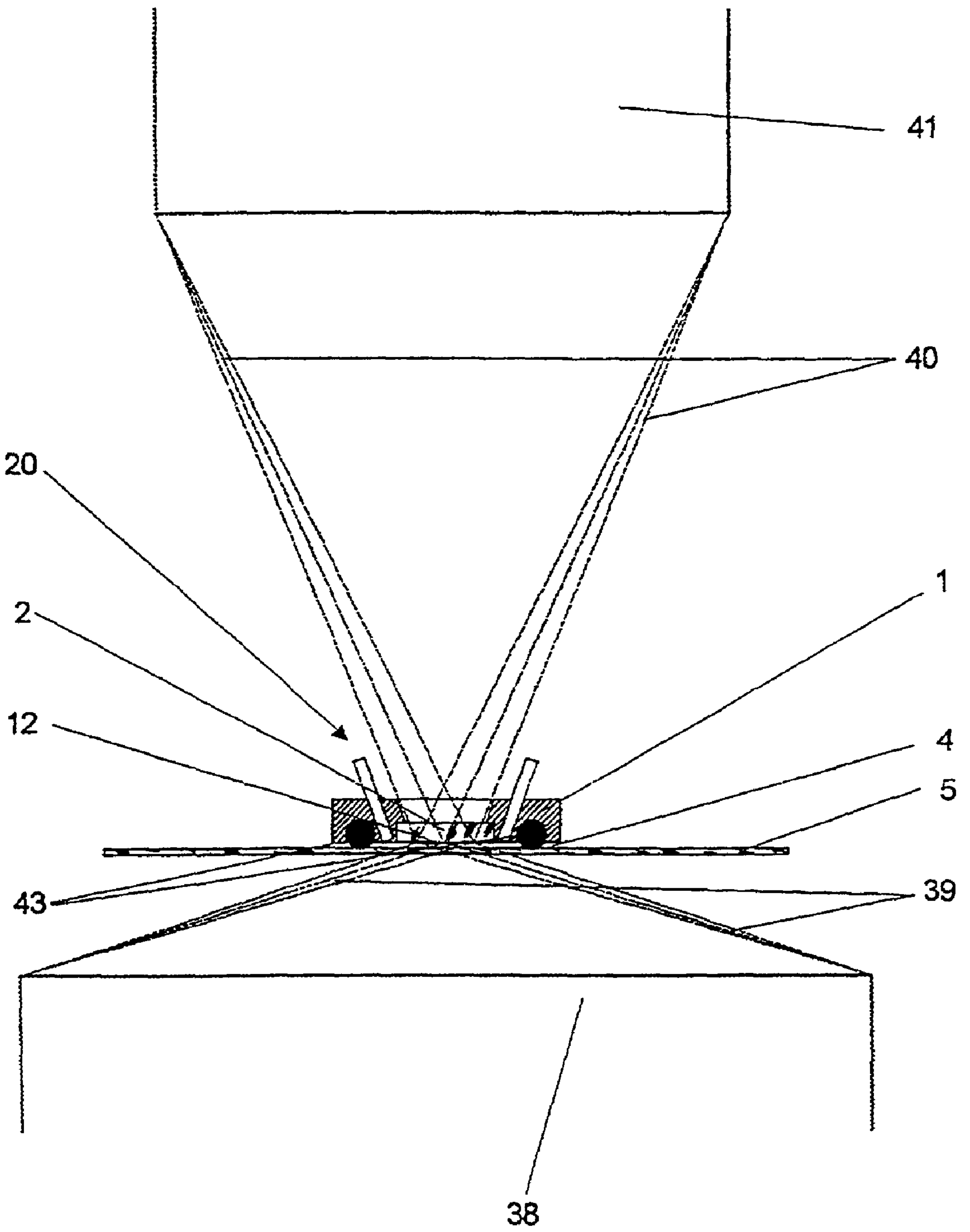
FIG. 13: a schematic representation of the optical path of rays through the device as per

In FIG. 13 the optical path of the rays across a further embodiment of device 20, wherein bearing surface 4 is connected in a releasable and sealing manner with chamber support 5 through an additional sealing surface 43, is shown for the dark field fluorescence representation of detection surface 12 of chip 2. Such as illustrated, the excitation light is directed across dark field mirror 38 to detection surface 12 along the optical path 39 of the excitation light. The fluorescence light coming from detection surface 12 is directed to a microscope objective 41 along the optical path 40 of the detection light. Thereby, the distance between dark field mirror 38 and detection surface 12 is in this example approximately 4.6 mm, and the distance between detection surface 12 and microscope objective 41 is approximately 22.0 mm.

Figure 14:
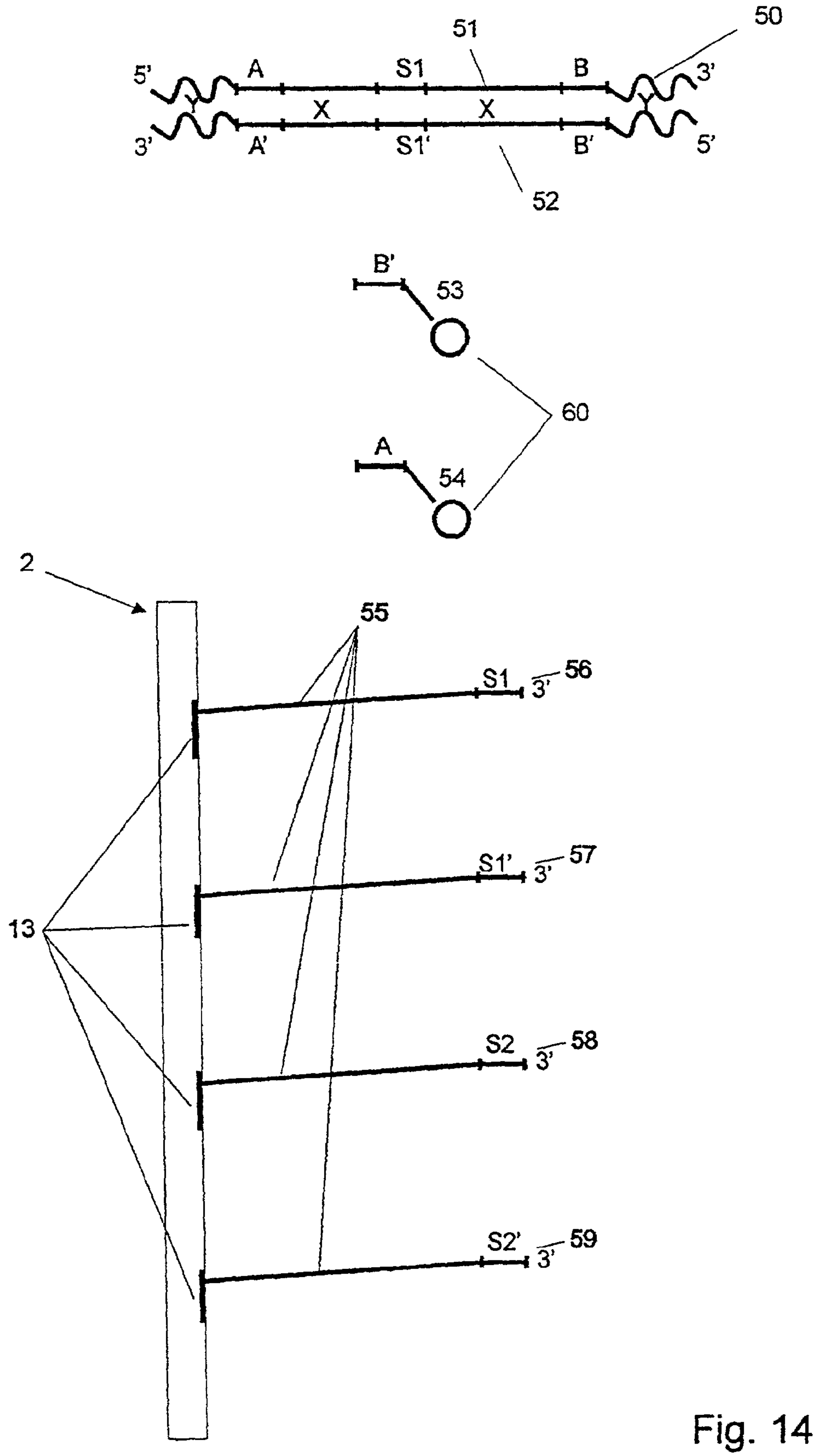

The optical readout on the surface of chip 2 of the interaction signal between the target DNA 50 and probe DNA 56, 57, 58, 59 shown in FIG. 14, can ensue online due to the construction of device 20.

Chip 2 is supported in chamber body 1 in such a manner that it can be light-radiated in a wide spatial angle, so that the hybridization can be traced online or in situ by means of the marked probes 56, 57, 58, 59, e.g. by fluorescence measurements. The arrangement and size of temperature sensor 16 and quadrupole 19 is so configured that the optical path for the online detection or the subsequent in situ detection will not be disturbed, and the detection of the interactions on spot 13 can be evaluated by all forms of the optical detection or spectroscopy (e.g. photometry, differential photometry, confocal fluorescence measurement, dark field fluorescence measurement, direct-light fluorescence measurement, etc.), whereby labels 60 and measurement method have to be matched up to one another.

In general, the detection method used for detecting an interaction is determined by the type of marker, which has been added to the target or probe molecules either prior to, subsequent to or during the reaction. As markers, for example, can also be used radioactive markers, chemiluminescent markers, enzymatically active groups and/or haptens. The detection of the hybridization can in this case correspondingly ensue by detecting an enzymatic activity or a chemical reaction such as, for example, a silver precipitation reaction.

FIG. 14 shows the schematic representation of chip 2, which carries primers 54 (A) und 53 (B'), whereby these correspond to the specific sequence range of target DNA 50, hence the sequences A, X, S1, X, B and B', X, S1', X, A'. Sequences A and B, and A' and B', respectively, define that range of target DNA 50, and of the one-stranded AB target DNA 51 and A'B' target DNA 52, respectively, which is identical for all species. In the example, probes 56, 57, 58 and 59 are immobilized through spacers 55, which probes carry sequences specific for the target DNA 50 of a defined origin, this means that in the example shown, only the probes 56 and 57 with the sequences S1 and S1' hybridize to the amplification products of target DNA 50 (shown in FIG. 15). Whereas at probes 58 and 59 with the sequences S2 and S2', no hybridization takes place.

The primers 53 and 54 bear, for example, a fluorescence marker 60 which can be incorporated into the secondary amplification products 61 and 62 by means of the amplification process, whereby the hybridization can be detected at the probes 56 and 57 during the amplification by fluorescence measurement, so that the decision is made possible whether target DNA 50, between the sequence ranges A and B, and A' and B', respectively, features the sequence S1 or S1' and/or the sequence S2 or S2'.

Since the probe sequences can, for example, be specific for a certain species, the presence of a certain species in a sample can be proven with this method.

Figure 15:
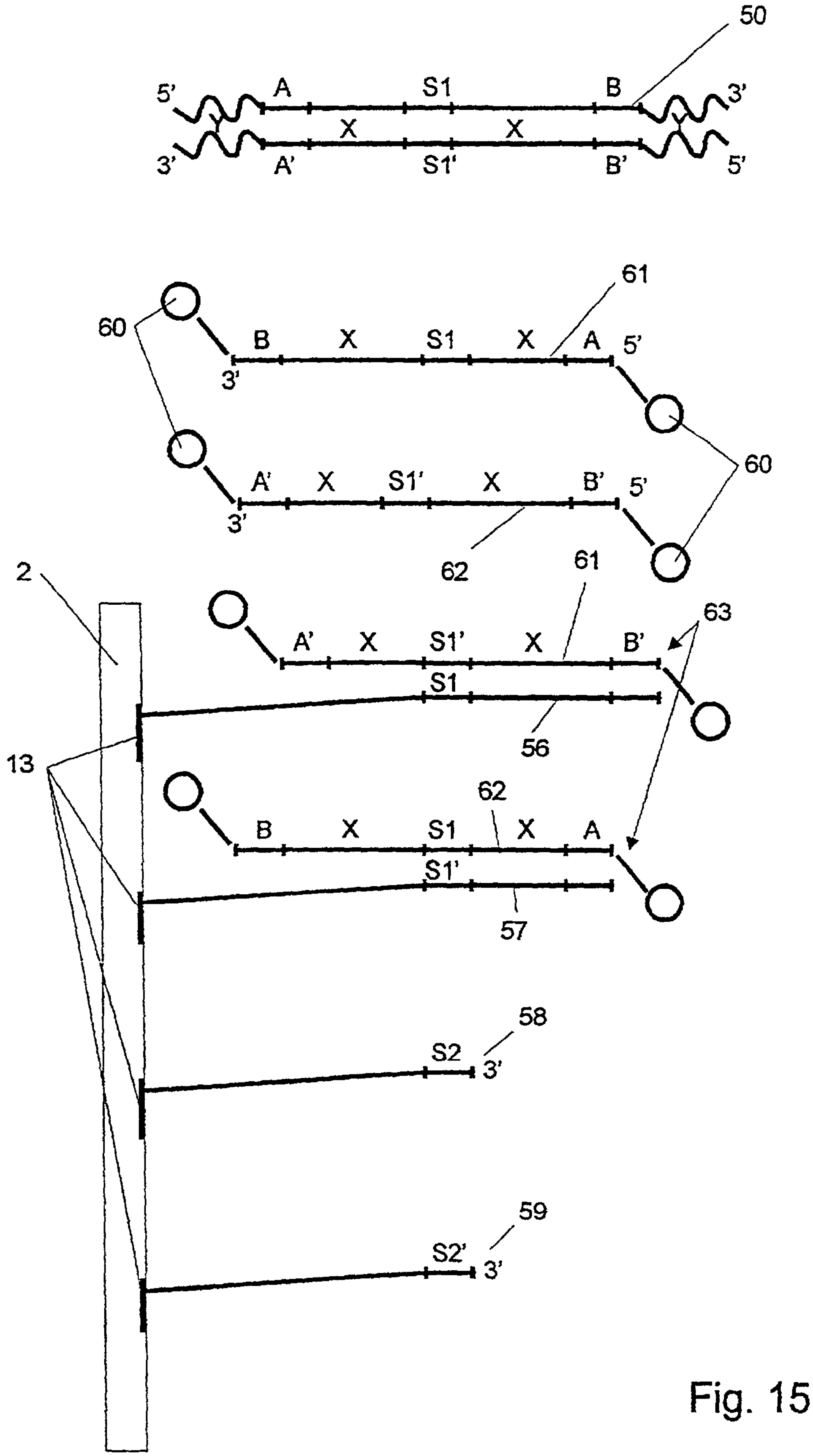

FIG. 15 shows a schematic representation of the secondary and tertiary amplification products 61, 62 and 63, which can be generated by means of device 20. As of the second reaction cycle, the amount of the secondary amplification product 61 and 62 is almost doubled within capillary gap 7 with each cycle, so that the concentration of the secondary amplification product is sufficient after several cycles so as to hybridize to probes 56, 57, which are immobilized on spots 13, an extension of probes 56, 57 taking place complementary to the second amplification product 61, 62. This tertiary amplification product 63 from the probes 56, 57 and the secondary amplification product 61, 62 can, for example, be detected by fluorescence detection, through a label 60 coupled to the used primers 53, 54.

In a first application example, the specific detection of individual microorganism species shall be described:

Chip 2 of device 20 in this example, is a DNA chip, and serves during or after the DNA amplification for detecting the amplification products and, if the case may be, for supplying solid phase-coupled DNA primers, as well (FIGS. 14 and 15). A sequence S1, which is specific for one species (e.g. *Escherichia coli*), is copied, for example, so often from a plurality of possible targets by means of the thermal amplification process (e.g. PCR) that the secure recognition of this sequence by hybridization at probes 56, 57, 58 and 59 and fluorescence measurement on detection surface 12 becomes possible. If several sequences are known which are in each case specific, e.g. for one species, one strain or one disease, and which are all between two conserved ranges identical in all cases, then all species, strains and diseases, respectively, can be detected at the same time with only one thermal amplification reaction in device 20 by immobilization of the corresponding probes on chip 2. Through the use of several primer pairs 53, 54, the application range may be expanded. The fluorescence detection of the tertiary amplification products 63 ensues in the simplest case by fluorescence marking 60 of primers 53, 54. Other marking types such as, for example, intercalators, radioisotopes, FRET systems, fluorescence-marked nucleotides, etc., are thereby not excluded.

The molecular-biological process occurring in device 20, shall be described in the following with reference to FIGS. 14 and 15.

The target DNS 50 originating from a biological sample, is placed into the sample reservoir (capillary gap) 7, together with primer 53, 54, which can be labeled 60. The spots 13 of chip 2 on detection surface 12 carry, on spacers 55, probe DNA with the sequences S1, S1', S2, S2', etc., which are characterized in that they can be complementary to those present in target DNA 50. In the example shown in FIG. 14, target DNA 50 contains sequences, which are complementary to the probes 56 and 57. Each sequence S1, S1' and S2, S2' etc., of the probes (56, 57, 58, 59) has been selected so that it is specific for a defined statement of problems. If, for example, certain pathogens are to be detected by means of device 20, S1 and S1' are to be specific for the pathogen *Bacillus cereus*, S2 and S2' for the pathogen *Campylobacter jejuni*, etc. If only the pathogen *Bacillus cereus* is present in a sample of faeces, then a target DNA 50 only containing the sequences S1 and S1' will be present in the liquid sample after an appropriate processing of the sample. To bring same now, in a detectable manner, to the hybridization on detection surface 12, the number of the copies of target DNA 50 in general has to be significantly increased. Therefore, a specific noise-canceling DNA amplification method is carried out in sample reservoir (capillary gap) 7. For this purpose, two primers 53, 54 with the sequences A and B', which are identical for all pathogens are selected, embracing all pathogen-specific probe sequences (S1, S2, S3 . . . ) (as the sequences S1 and S1', respectively, are embraced by the sequences A and B', such as it is shown in FIG. 14). Then, as in the case of PCR, target DNA 50 is denaturized at about 90° C., primers 53, 54 anneal to B and A', respectively, at about 65° C., and a primer extension reaction is carried out at about 70° C., making target DNA 51, 52 double-stranded. The product then obtained is the primary amplification product with the sequences A, X, S1, X, B, Y and B', X, S1', X, A', Y, respectively. The denaturizing, annealing and extension cycle is repeated, whereupon the secondary amplification product 61, 62 is obtained (cf. FIG. 15). By repeating the amplification cycle several times, the number of the secondary amplification products 61, 62 will almost double. Thereby, the concentration of DNA containing the sequences S1 and S1' increases in such a way that a secure detection of the hybridization on probes 56, 57 becomes possible. DNA still present in the liquid sample and binding to the spots in an unspecific manner, is not covered by the amplification process, the selectivity of the entire method being thereby considerably increased.

Thus, *Bacillus cereus* is detected in a highly specific and highly sensitive manner. Instead of the PCR protocol, other amplification methods can likewise be used.

Through the integration of device 20 for duplicating and characterizing nucleic acids into assay system 200 (FIG. 11), there is the possibility of conducting the reprocessing processes of samples in an automatic and continuous manner.

In a second application example, a parallel detection of bacterial pathogens in samples of faeces shall be described:

In this example, chip 2 of device 20 is a DNA chip and serves for the parallel detection of several bacterial pathogens in human or animal samples of faeces.

From each sample of faeces, the overall DNA is segregated by means of standard techniques (e.g. by means of the kit intended for this purpose of the Qiagen company). The DNA is adsorbed in a volume suited for use in device 20 of a standardized, if the case may be, commercially available, buffer system, in which a PCR amplification can be carried out. Apart from the buffer component, this system contains at least one thermostable polymerase, a possibly isomolar mixture of the four natural deoxynucleotide triphosphates, a divalent salt, possibly components for enhancing the PCR effectiveness, as well as components for labeling the PCR products (e.g. fluorescence-marked, biotin-marked or similarly marked deoxynucleotide triphosphates).

For detecting the organisms, a chip 2 is used, on the surface of which oligonucleotide probes 56, 57, 58, 59 are immobilized, which are complementary to one or more variable ranges of the 16S rRNA genes and/or the 23S rRNA genes and/or to the inner-genetic ranges between the 16S and 23S rRNA gene of various organisms to be detected. Probes 56, 57, 58, 59 are, for example, directed against one or more of the corresponding sequences of *Aeromonas* spec. and/or *Bacillus cereus* and/or *Campylobacter jejuni* and/or *Clostridium difficile* and/or *Clostridium perfringens* and/or *Plesiomonas shigelloides* and/or *Salmonella* spec. and/or *Shigella* spec. and/or *Staphylococcus aureus* and/or *Tropheryma whippelii* and/or *Vibrio cholerae* and/or *Vibrio parahaemolyticus* and/or *Yersinia enterocolitica*.

The oligonucleotide probes 56, 57, 58, 59 are arranged in spots 13, so that every single spot 13 contains a plurality of oligonucleotide probes (e.g. the probe 56) of the same sequence. The immobilization of probes 56, 57, 58, 59 either ensues at their 3' end or at the 5' end or an internal position, respectively, the 3' end of probes 56, 57, 58, 59 possibly being blocked by amination, so that it cannot serve as a substrate for DNA polymerases.

The selection of probes 56, 57, 58, 59 is made so that, for one, each of the probes features a high sequence-specificity for the organism to be detected and, for another, motives exist in the genomes of the germs at a minor distance from the bonding point of the specific probes, which have the same sequence for all or for groups of the organisms to be detected.

Universal primers 53, 54 are directed against these motives. These primers 53, 54 are suited to amplify by means of PCR in all organisms to be detected, a sequence segment containing the bonding point of the probes immobilized on chip 2. These primers 53, 54 are added to the DNA which has been segregated from the sample of faeces and have been adsorbed in the amplification solution (liquid sample 19). If the case may be, primer 53, 54, which specifies the synthesis of the strand during the subsequent PCR amplification, and which contains the sequence which is complementary to the sample immobilized on chip 2, can be added as a marked component.

The amplification mixture is filled into device 20 provided with a labeled chip 2. The solution in device 20 is subjected to a cyclic temperature regimen so that target DNA 50 is amplified according to a typical PCR mechanism and possibly is simultaneously marked. After a sufficient amplification, a hybridization step is carried out, wherein the target sequences amplified with the universal primers 53, 54, hybridize with the specific probes 56, 57, 58, 59 immobilized on chip 2.

After completion of the reaction, a washing step takes place, wherein DNA molecules, which are not linked to the chip or are not specifically bound, are removed.

Subsequently, the detection of the marking remaining on chip 2 takes place. Organisms present in the sample of faeces are identified through the marking of the sample spots 13 on chip 2, which are specific for them.

For obtaining liquid samples, for example, from samples of faeces or tissues, a plurality of processing steps are necessary. Cells have to be decomposed, proteins, lipids and solid substances have to be segregated, and the DNA has to be processed and purified. The enzymes, primers and other substances necessary for the use of the device, have likewise to be added to liquid sample 19. These steps can be carried out in an automatic and continuous manner by installing device 20 for duplicating and characterizing nucleic acids into assay system 200, which, inter alia, is composed of pumps and valves 28, which move and control the liquids, of filters and reaction chambers (conditioner 27), in which the separate process steps are successively carried out, and of storage tanks 29 furnishing the chemicals required for this purpose (shown in FIG. 11). The samples thereby are filled in for being conditioned through the overall inlet 25 by a pipetting robot 37 of a standard feed system not shown in detail. The samples processed by assay system 200 arrive at device 20 through inlet 81, so that the duplication and characterization of the nucleic acids of the samples can be carried out in an automated manner. The entire process is monitored by a control computer 35, which is connected to electronic controllers and control devices 21, 22, 31, 32 via a computer bus 36.

All of the features described in the description, the following claims and the drawings, can be invention-relevant taken alone or in any arbitrary combination thereof.

List of Reference Numerals

| | |
|---|---|
| 1 | chamber body |
| 2 | chip |
| 3 | sample chamber |
| 4 | bearing surface |
| 5 | chamber support |
| 6 | gas reservoir |
| 7 | capillary gap |
| 81 | inlet |
| 82 | outlet |
| 9 | gas reservoir nose |
| 11 | recess |
| 12 | detection surface |
| 13 | spot |
| 14 | connecting surfaces |
| 15 | conducting path |
| 16 | temperature sensor |
| 17 | heating elements |
| 171 | resistance lines |
| 18 | quadrupole |
| 181 | electrodes |
| 19 | liquid sample |
| 20 | device |
| 21 | temperature controller |
| 22 | mixing control |
| 23 | electric lines for temperature control |
| 24 | electric lines for quadrupole control |
| 25 | overall inlet |
| 26 | waste receptacle |
| 27 | conditioners |
| 28 | pumps/valves |
| 29 | storage tank |
| 30 | connecting tubes |
| 31 | conditioner control |
| 32 | automat control |
| 33 | electric lines for conditioner control |
| 34 | electric lines for automat control |
| 35 | control computer |
| 36 | computer bus |
| 37 | pipetting automat (pipetting robot) |

-continued

List of Reference Numerals

| | |
|---|---|
| 38 | dark-field mirror |
| 39 | optical path of excitation light |
| 40 | optical path of detection light |
| 41 | microscope objective |
| 42 | edge |
| 43 | sealing surface |
| 50 | target DNA |
| 51 | AB Target DNA |
| 52 | A'B' Target DNA |
| 53 | primer B' |
| 54 | primer A |
| 55 | spacer |
| 56 | probe S1 |
| 57 | probe S1' |
| 58 | probe S2 |
| 59 | probe S2' |
| 60 | label, fluorescence marking |
| 61 | secondary amplification product |
| 62 | secondary amplification product |
| 63 | tertiary amplification product |
| 200 | assay system |
| 1416 | connecting surfaces of temperature sensor |
| 1417 | connecting surfaces of heater |
| 1418 | connecting surface of quadrupole |
| 1516 | conducting path of temperature sensor |
| 1517 | conducting path of heater |
| 1518 | conducting path of quadrupole |
| A-A | cutting plane |
| B-B | cutting plane |
| C-C | cutting plane |
| D-D | cutting plane |
| E-E | cutting plane |

The invention claimed is:

1. A device for duplicating and characterizing nucleic acids in a reaction chamber, comprising a reaction chamber defined by:

a chamber support having an optically permeable first surface facing the reaction chamber;

a chamber body sealingly and unreleasably placed on the chamber support and including:

a recess having an edge configured to support a chip; and an inlet providing fluid communication between the reaction chamber and an environment external to the reaction chamber; and a rigid optically permeable chip, sealingly supported by the edge of the recess, and having a second surface facing the reaction chamber, the second surface having an array of multiple different polynucleotide probes immobilized thereon, wherein the first and second surfaces are substantially parallel.

2. The device of claim 1, further comprising a temperature adjustment means connected with the chamber support and adapted to permit a rapid temperature control of the continuous cavity.

3. The device of claim 2, wherein the temperature adjustment means are situated on a side of the chamber support facing towards the chamber body.

4. The device of claim 2, wherein the temperature adjustment means are configured such that the optical transparency of the chip remains unaffected at least at the array.

5. The device of claim 4, wherein the temperature adjustment means comprise micro-structured heating elements.

6. The device of claim 1, wherein the chamber support comprises systems for thoroughly mixing a liquid sample, the systems being configured such that the chip remains optically transparent at least at the array; and a quadrupole system, adapted to induce an electro-osmotic flow, is associated with the chamber support.

7. The device of claim 6, wherein the quadrupole system includes gold-titanium electrodes.

8. The device of claim 1, wherein the chamber support and the chamber body consist of at least one of glass, synthetic material, and optically permeable synthetic materials.

9. The device of claim 1, wherein the chamber support consists of a thermally conducting material.

10. The device of claim 1, wherein the chip consists of optically permeable materials including at least one of glass, borofloat glass, quartz glass, monocrystalline $CaF_2$, sapphire, PMMA and silicon.

11. The device of claim 1, wherein the recess in the chamber body is an optically permeably conical recess aligned with the array.

12. The device of claim 1, wherein the chamber body includes an inlet and an outlet spatially separate from each other, for charging the reaction chamber.

13. The device of claim 12, wherein the inlet and the outlet are arranged unilaterally to the chip and are separated by a gas reservoir nose.

14. The device of claim 1, wherein the chamber body is sealingly and unreleasably connected with the chamber support by at least one of an adhesive and weld connection.

15. The device of claim 1, wherein the probes are immobilized through spacers.

16. The device of claim 1, wherein the reaction chamber is adapted to allow characterization by at least one of optical detection and spectroscopy.

17. The device of claim 1, wherein the chip is adapted to allow characterization by a silver precipitation reaction.

18. The device of claim 1, wherein the first surface is held opposite to the second surface by the chamber body.

* * * * *